United States Patent [19]

Smith et al.

[11] 4,286,874
[45] Sep. 1, 1981

[54] DIFFRACTOMETER

[75] Inventors: Francis H. Smith, York; Richard W. Gale, Malton, both of England

[73] Assignee: Vickers Limited, London, England

[21] Appl. No.: 29,124

[22] Filed: Apr. 11, 1979

[30] Foreign Application Priority Data

May 31, 1978 [GB] United Kingdom ............... 14434/78

[51] Int. Cl.³ ............................................. G01N 21/00
[52] U.S. Cl. ..................................... 356/338; 350/89
[58] Field of Search ................... 350/89; 356/336, 338

[56] References Cited

U.S. PATENT DOCUMENTS 2,812,686  11/1957  Sinclair ............................ 350/89 X
3,563,660  2/1971   Soloway et al. ..................... 356/336

FOREIGN PATENT DOCUMENTS 1130969 of 0000 United Kingdom .
1316752 of 0000 United Kingdom .

OTHER PUBLICATIONS

Timbrell, "Alignment of Respirable Asbestos Fibres by Magnetic Fields", *Annals of Occupational Hygiene* vol. 18, p. 399.

*Primary Examiner*—John K. Corbin
*Assistant Examiner*—Matthew W. Koren
*Attorney, Agent, or Firm*—Browdy and Neimark

[57] ABSTRACT

A diffractometer comprises means for illuminating a specimen plane and a lens for converging rays diffracted from the specimen plane. In order that existing optical apparatus may readily be adapted for use as a diffractometer, the illuminating means (12a, 12b, 13, 14) is arranged to illuminate the specimen plane (0-0') at an acute angle, and a positive lens (15) having its principal axis normal to the specimen plane (0-0') is arranged to converge rays diffracted normally from the specimen plane. The apparatus is particularly susceptible to compact construction by arranging, in successive order from the specimen plane (0-0'), a field stop (17), the positive lens (15), an aperture stop (16) and a photodetector (19), which parts advantageously can form a modular assembly. The invention is particularly applicable to converting microscopes for use as diffractometers, which then are suitable for use in monitoring respirable air-born fibers.

21 Claims, 1 Drawing Figure

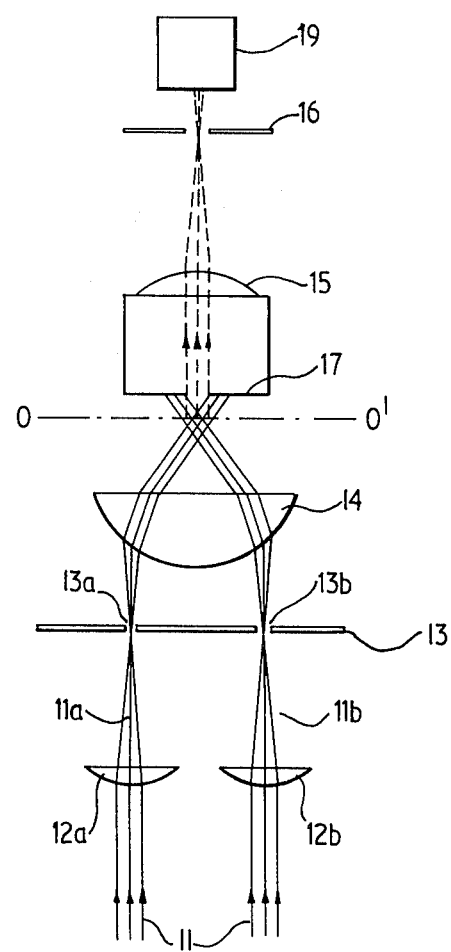

DIFFRACTOMETER

This invention relates to diffractometers, and is particularly, although not exclusively, concerned with particle counting.

In "Alignment of Respirable Asbestos Fibres by Magnetic Fields", published in "Annals of Occupational Hygiene", Volume 18, pp 299-311, V. Timbrell describes an optical system for monitoring air-borne fibers which have been brought into alignment by application of a magnetic field. Essentially this system is a simple form of diffractometer wherein the light-scattering (diffracting) specimen is illuminated by a normally-incident collimated beam of light and the light which is thereby scattered along a pre-selected path making a specified angle with the incident beam is photo-electrically detected by any appropriate device, e.g. a photomultiplier.

However, a much more frequently used instrument for respirable particle monitoring is the optical microscope so, in the interests of economy, it would be advantageous to find a convenient way of converting this instrument into a diffractometer as and when required.

Perhaps the most obvious course would be to provide the normally-incident collimated beam by a small illuminated aperture at the center of the microscope condenser's first focal-plane, and thereafter to select the required diffracted beam by a similar aperture at an appropriate off-axis position at the microscope objective's rear focal plane. Unfortunately, this procedure is impracticable in that microscope objectives having a numerical aperture (NA) sufficient to accept typical preselected angles of diffraction (often as high as 30°) lack the lateral field of view (e.g. 4 mm. diameter) required to sense a statistically significant number of particles.

In co-pending application Ser. No. 29,125, filed on, even date herewith, of Dr. F. H. Smith (one of the present inventors), there is disclosed a diffractometer comprising means for illuminating a specimen plane at an acute angle thereto, and a positive lens having its principal axis substantially normal to the specimen plane, for converging rays diffracted substantially normally from the specimen plane.

Such a diffractometer may be provided by suitably modifying a microscope (e.g. a photo-electric microscope), and that application is also concerned with providing means for so modifying a microscope, particularly for use in particle monitoring methods as described in the above paper by V. Timbrell, to which paper the reader's attention is directed. For further information, the reader's attention is directed to the above-mentioned co-pending application of Dr. F. H. Smith.

The present invention is concerned with further improving the diffractometer as disclosed in Dr. Smith's co-pending application, such that it is susceptible to particularly compact construction, and hence particularly suitable for use in modifying a microscope for use as a diffractometer.

According to the present invention, there is provided a diffractometer comprising: means for illuminating a specimen plane at an acute angle thereto; a positive lens having its principal axis substantially normal to the specimen plane, for converging rays diffracted substantially normally from the specimen plane; a field stop, adjacent the specimen plane, for restricting the light which is converged by the positive lens; an aperture stop, downstream of the positive lens, for limiting the light rays converged by the positive lens to those diffracted substantially normally to the specimen plane; and a photo-electric detection means, downstream of the aperture stop, for detecting light from the positive lens.

The invention is also concerned with methods of detecting a light diffracting specimen by employing diffractometers in accordance with the invention, and with providing means for modifying a microscope for use as a diffractometer. Diffractometers in accordance with the invention may be particularly suitable for use in methods due to Timbrell, such as mentioned above.

For a better understanding of the invention and to show how the same may be carried into effect, reference will now be made, by way of example, to the accompanying diagrammatic drawing, the single FIGURE of which illustrates an embodiment of the invention.

In the drawing, a microscope (e.g. a photo-electric microscope) has been modified to serve as a diffractometer. The modification comprises a substage (optionally removable) which is for illuminating a specimen plane O-O' and comprises two lenses 12a and 12b, a diaphragm 13, and a condenser 14. Further modifications include a positive lens 15, an aperture stop 16, a field stop 17, and a photo-detector 19. The microscope may be modified to serve as a diffractometer as and when required.

An illuminating beam 11 is brought to two foci by the lenses 12a and 12b, which foci are centered on corresponding holes 13a and 13b in the substage diaphragm 13. The substage condenser 14, with its first focal plane at the diaphragm 13, converges the pair of light pencils 11a and 11b formed from the beam 11 onto the specimen plane O-O' at a pre-selected angle to the normal, defined by the positions of the diametrically opposed holes 13a and 13b. It will be appreciated that this arrangement provides a directional illumination of the specimen plane O-O', and in particular, illumination substantially in one plane. Fibrous specimen particles aligned, say, perpendicularly to the plane of the diagram preferentially diffract the obliquely incident light through a continuous range of angles in planes parallel to the diagram. Dashed lines indicate the normally diffracted portion of this light which is selected by the low power objective lens 15 in association with a central hole in the stop 16 at the rear focal plane of the lens 15. The field stop 17 adjacent the specimen plane O-O' serves to define the diffracted light beam which is converged by the objective lens 15, and the aperture stop 16 serves to limit the detected light rays converged by the lens 15 to those diffracted substantially normally to the specimen plane, which rays pass through the hole in the stop 16 onto the photo cathode of the photo-detector 19.

In order to implement methods as described by Timbrell, it is necessary to provide relative rotation of the specimen relative to the apertures in the diaphragm 13. This is readily achieved by supporting the specimen upon a circular, rotatable stage, as normally provided by conventional polarizing microscopes. Alternatively, it would be possible to rotate the diaphragm 13 together with the associated lenses 12a and 12b (and optionally also the condenser 14), but the former method is presently preferred. In either case, the means for causing the rotation may conveniently comprise an electric motor which can operate continuously to rotate the rotatable stage and/or the diaphragm 13 with associated parts.

It will be understood that provision of the two illuminating beams 11a and 11b is not an essential feature of the invention, as either beam alone would serve. However, there would be a corresponding reduction of signal level at the detector 19, and the resulting asymmetry of illumination might lead to corresponding asymmetry in response relative to specimen versus diaphragm rotation. However, this alternative single beam mode of operation would make one of the lenses 12a and 12b superfluous.

As a modification to the illustrated arrangement, each of the apertures 13a and 13b could be in the form of a slot which extends radially of the diaphragm 13, and therefore also radially in relation to the principle axis of the condenser 14. This is because, particularly when the diffractometer is used in methods as described by Timbrell, and possibly also in other applications, the precise angle or angles of incidence of the light on the specimen plane O–O' is not critical. Thus, by allowing a range of a few degrees for the angle of incidence, it is possible to gain a light advantage—i.e. more light is allowed through the diffractometer. For similar reasons, the aperture in the stop 16 could also be in the form of a slot, rather than a circular aperture.

The photodetector 19 may conveniently be a solid-state silicon photo-detector, and the photodetector 19, the aperture stop 16, the objective lens 15 and the field stop 17 may conveniently be provided as a modular assembly. Then, to convert the microscope to a diffractometer, the conventional objective lens and its mounting are simply removed from the optical path of the microscope, and the modular assembly containing the new objective lens 15 and the photo-detector 19 is fitted in its place. The modular assembly containing the lens 15 is conveniently screwed into one station of a microscope's objective changer, e.g. a station of a rotatable nosepiece. Thus, with the illustrated illuminating arrangement being exchangeable with a conventional microscope illuminating arrangement, the microscope may readily be convertible between use as a normal microscope and use as a diffractometer.

Although the lens 15 is described in the above as a microscope objective lens, it is not essential for the lens 15 to be so. It is merely necessary for the lens 15 to be a positive lens, which acts simply as a collector to converge rays diffracted substantially normally from the specimen plane O–O'.

The illustrated embodiment is suitable for use in particle counting methods as disclosed by Timbrell, where providing relative rotation between aligned fibers and the illuminating arrangement leads to an output signal from the photodetector 19, which signal has peaks and is indicative of the quantity of fiber in the specimen plane.

We claim:

1. A diffractometer comprising: means for illuminating a specimen plane at an acute angle thereto, the axis of the or each beam of illuminating light rays lying in a common plane; a positive lens having its principal axis substantially normal to the specimen plane, for converging rays diffracted substantially normally from the specimen plane; a field stop, adjacent the specimen plane, for restricting the light which is converged by the positive lens; an aperture stop, downstream of the positive lens, for limiting the light rays converged by the positive lens to those diffracted substantially normally to the specimen plane; and a photo-electric detection means, downstream of the aperture stop, for detecting light from the positive lens.

2. A diffractometer according to claim 1, wherein the illuminating means comprises a condenser arranged to receive a light beam substantially normal to the specimen plane and transmit the light beam across the specimen plane at said angle thereto.

3. A diffractometer according to claim 2, wherein the illuminating means comprises a diaphragm upstream of the condenser, the diaphragm being formed with at least one aperture offset from the principle axis of the condenser, for transmitting to the condenser a light beam which, after exit from the condenser, crosses the specimen plane at said angle thereto.

4. A diffractometer according to claim 3, wherein the diaphragm is formed with two apertures diametrically opposed about the principal axis of the condenser, for transmitting to the condenser two respective light beams which, after exit from the condenser, cross the specimen plane at said angle thereto.

5. A diffractometer according to claim 3, wherein each said aperture is in the form of a slot which extends radially in relation to the principal axis of the condenser.

6. A diffractometer according to claim 3, wherein the illuminating means comprises, upstream of the diaphragm, a respective lens for converging a light beam to a focus at the or each respective said aperture.

7. A diffractometer according to claim 1, including means for providing relative rotation between a specimen in the specimen plane and the illuminating means, about the principal axis of said positive lens.

8. A diffractometer according to claim 1, further including a rotatable nosepiece and first and second assemblies mounted thereon, which assemblies can be selectively positioned to view the specimen plane, such that the diffractometer may be used as a microscope when said first assembly is positioned to view the specimen plane and a diffractometer when said second assembly is positioned to view the specimen plane, wherein said field stop, positive lens, aperture stop and photo-electric detection means form part of said second assembly, whereby making the diffractometer selectively convertible for use either as a conventional microscope or as a diffractometer.

9. A diffractometer according to claim 1, wherein said illuminating means comprises a modular assembly which is removable from the diffractometer as desired.

10. A diffractometer according to claim 1, wherein said field stop, positive lens, aperture stop and photoelectric detection means form part of a modular assembly which is removable from the diffractometer as desired.

11. A diffractometer microscope selectively convertible for use as a diffractometer and as a microscope and comprising:
   a condenser arranged to receive at least one light beam substantially normal to a specimen plane and transmit the or each light beam across the specimen plane at an acute angle thereto;
   a diaphragm upstream of the condenser, the diaphragm being formed with a respective aperture offset from the principal axis of the condenser for transmitting to the condenser a respective said light beam which, after exit from the condenser, crosses the specimen plane at said angle thereto;
   a respective lens for converging a respective said light beam to a focus at a respective said aperture;

a positive lens having its principal axis substantially normal to the specimen plane, for converging rays diffracted substantially normally from the specimen plane;

a field stop, adjacent the specimen plane, for restricting the light which is converged by said positive lens;

an aperture stop downstream of said positive lens, for limiting the light-rays converged by said positive lens to those diffracted substantially normally to the specimen plane;

a photo-electric detection means for detecting light from said positive lens;

means for providing relative rotation between said specimen plane and said light beams about the principal axis of said positive lens; and a rotatable microscope nosepiece in which said positive lens, field and aperture stops, and photoelectric detection means are engaged as a removable modular assembly.

12. A method of detecting a light-diffracting specimen contained in a specimen plane, said specimen comprising asbestos fibers, the method comprising the steps of illuminating the specimen at an acute angle to the specimen plane, detecting light diffracted by the specimen normal to the specimen plane, and obtaining an electrical signal indicative of the quantity of fiber present in the area of the specimen plane detected by the diffractometer, wherein at least said illuminating and detecting steps are carried out by means of a diffractometer according to any one of claims 1–11.

13. A method of detecting a light-diffracting specimen contained in a specimen plane, the method comprising the steps of illuminating the specimen at an acute angle to the specimen plane, and detecting light diffracted by the specimen normal to the specimen plane, by means of a diffractometer according to claim 1.

14. A method according to claim 13, wherein the specimen comprises fibers.

15. A method according to claim 14, wherein said fibers are air-borne respirable fibers.

16. A method according to claim 15, wherein said fibers are asbestos fibers.

17. A method according to claim 14, wherein said fibers are brought into alignment by application of a magnetic field.

18. A method according to claim 17, wherein said fibers are asbestos fibers.

19. A method according to claim 14, including the step of obtaining an electrical signal indicative of the quantity of fiber present in the area of the specimen plane detected by the diffractometer.

20. A method according to claim 19, wherein said fibers are asbestos fibers.

21. A method according to claim 14, wherein said fibers are asbestos fibers.

* * * * *